(12) United States Patent
Nelson

(10) Patent No.: US 10,974,047 B2
(45) Date of Patent: Apr. 13, 2021

(54) ADJUSTABLE TMJ HEADBAND

(71) Applicant: Lisa C. Nelson, Rockredge, FL (US)

(72) Inventor: Lisa C. Nelson, Rockredge, FL (US)

(*) Notice: Subject to any disclaimer, the term of this patent is extended or adjusted under 35 U.S.C. 154(b) by 243 days.

(21) Appl. No.: 16/192,481

(22) Filed: Nov. 15, 2018

(65) Prior Publication Data
US 2019/0143114 A1  May 16, 2019

Related U.S. Application Data

(60) Provisional application No. 62/587,071, filed on Nov. 16, 2017.

(51) Int. Cl.
*A61N 1/36* (2006.01)
*A61N 1/04* (2006.01)
*A61N 5/06* (2006.01)
*A61H 39/00* (2006.01)
*A61H 39/02* (2006.01)

(52) U.S. Cl.
CPC ......... *A61N 1/36021* (2013.01); *A61H 39/00* (2013.01); *A61H 39/002* (2013.01); *A61H 39/02* (2013.01); *A61N 1/0456* (2013.01); *A61N 1/0484* (2013.01); *A61N 1/36031* (2017.08); *A61N 5/0619* (2013.01); *A61H 2201/0157* (2013.01); *A61H 2201/0192* (2013.01); *A61H 2201/10* (2013.01); *A61H 2201/165* (2013.01); *A61H 2201/1607* (2013.01); *A61H 2201/169* (2013.01); *A61H 2201/1609* (2013.01); *A61H 2201/5023* (2013.01); *A61H 2201/5046* (2013.01); *A61H 2205/02* (2013.01); *A61H 2205/022* (2013.01); *A61H 2205/028* (2013.01); *A61H 2205/04* (2013.01); *A61H 2205/062* (2013.01); *A61N 1/3603* (2017.08); *A61N 2005/0626* (2013.01); *A61N 2005/0647* (2013.01); *A61N 2005/0651* (2013.01); *A61N 2005/0662* (2013.01); *A61N 2005/0663* (2013.01)

(58) Field of Classification Search
CPC .............. A61N 1/36021; A61N 1/0456; A61N 5/0619; A61N 1/0484; A61N 1/36031; A61H 39/00; A61H 39/02
USPC ............................................................ 607/3
See application file for complete search history.

(56) References Cited

U.S. PATENT DOCUMENTS

2015/0202428 A1* 7/2015 Miller .................. A61N 1/0456 607/141
2018/0056065 A1* 3/2018 Muller ............... A61N 1/36021

* cited by examiner

*Primary Examiner* — Amanda K Hulbert
*Assistant Examiner* — Philip C Edwards
(74) *Attorney, Agent, or Firm* — Wilson Daniel Swayze, Jr.

(57) ABSTRACT

A device for treatment of temporomandibular joint (TMJ) disorder is disclosed. The device combines the benefits of LED therapy with the stimulation and pain relieving qualities of a transcutaneous electrical nerve simulation (TENS) unit for the TMJ treatment. The device comprises an adjustable headband strap, to be worn by a user. The adjustable strap could consist of a shoulder extension, and face and head extensions, which offers a combined TENS and red LED contact points. The TENS connectors connect a remote TENS controller to the headband strap and the headband strap to the user's skin for the optimum stimulation. Further, the device comprises acupuncture points for skin rejuvenation. A temple strap formed integral to the headband strap consists of a TENS electrode and LED unit and for the adjustment of the headband.

20 Claims, 12 Drawing Sheets

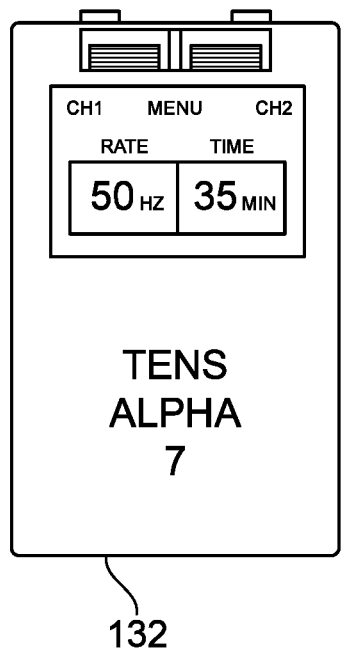
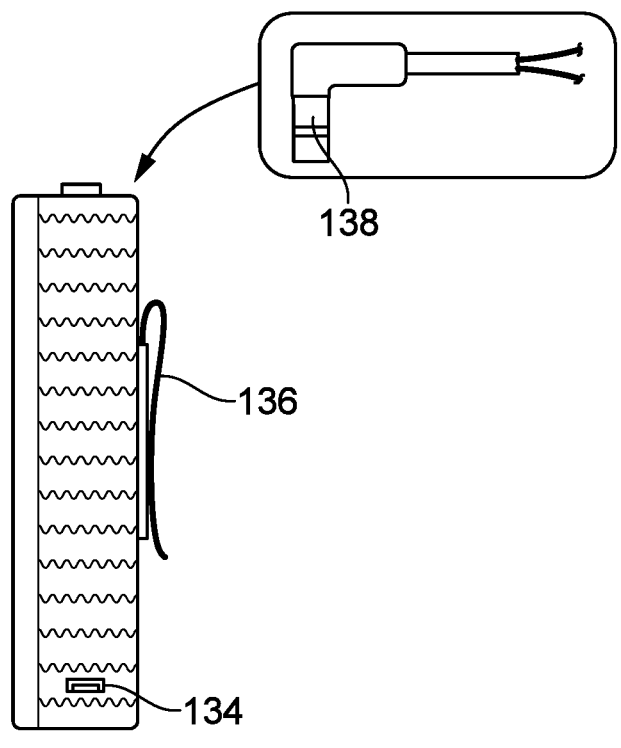
FIG. 7A
FIG. 7B

ADJUSTABLE TMJ HEADBAND

BACKGROUND OF THE INVENTION

A. Technical Field

The present invention generally relates to healthcare device. More specifically, the present invention relates to a device for treatment of temporomandibular joint disorder.

B. Description of Related Art

Temporomandibular joint disorders are commonly known as TMJ. These disorders frequently exhibit symptoms of pain and limited mobility of the jaw and the surrounding tissue. TMJ affects people of all ages and the discomfort caused could range from mild to severe. According to experts, nearly ten million Americans suffer from some level of TMJ. The causes of TMJ are often indeterminable, but sometimes they are attributed to medical and dental issues, trauma to the joint or joints, arthritis, grinding to the teeth and many other causes. Regardless of the reason, the resulting TMJ pain and discomfort forces many people to seek medical treatments for relief. Temporary treatments could range from changing eating habits such as resorting to soft foods, applying ice, avoiding extending the jaw and mouth, over the counter medications for pain, and other treatments that may provide temporary relief. Permanent treatments may include dental work to correct the bite, surgical and orthopedic methods that could be challenging and expensive. In many cases, with a physician's help, TMJ will resolve itself on its own without the intervention of surgery or invasive procedures.

Generally, relieving the pain resulting from a temporomandibular joint disorder is often the most suitable solution for the condition. Pain-relieving medications could often help, and pain reducing procedures are often employed to bring relief to patients suffering from this disorder.

TENS therapy or transcutaneous electrical nerve simulation could be an ideal solution to the pain and discomfort associated with persons afflicted with TMJ. TENS has been a successful therapeutic principal for decades and has been proven to reduce pain and promote healing. TENS units are transportable and could be applied directly to the skin and the source of the pain in many cases. LED light therapy encourages the restoration of the skin and is often used in conjunction with TENS therapy.

The red light (LED) therapy is very popular today, especially for improving skin appearance and anti-aging treatments. The effects of the red (660 nm wavelength) light from cool operating LEDs has some unique benefits, resulting from the stimulation of the frequency of the typical human cell. Further, placing the red LEDs with the known acupuncture points generates additional benefits.

Further, TENS therapy employs electrical pulses, which is conducted into the skin to stimulate the nerves for therapeutic purposes. TENS employs electrodes to conduct transcutaneously applied electrical pulses into the skin and to the nerves below the skin to excite them. This excitation can block pain and promote rehabilitation of the damaged tissue.

Currently, the red light therapy and TENS electrical pulses are not usually performed at the same time. Additionally, the typical red light treatment of the skin is broadly distributed rather being localized at the acupuncture points. This broad application generally forces treatment to a dermatologist office or other medical center.

Therefore, there is a need for an improved device that can be used in the treatment of the TMJ pain through the use of a combined treatment capability and portable enough to use like as a headband.

SUMMARY OF THE INVENTION

The present invention generally relates to healthcare device. More specifically, the present invention relates to a device for treatment of temporomandibular joint disorder.

The adjustable headband device is a solution for combining the benefits of LED therapy with the stimulation and pain relieving qualities of a TENS unit for the TMJ treatment. The device is completely portable and wearable. The adjustable headband strap of the headband device could be worn while doing daily tasks. The device straps on to the head with a comfortable expandable/adjustable headband strap. In an embodiment, adjustment connectors are located at the front and backside of the headband device that could allow the user or wearer to adjust the size of the headband.

In an embodiment, the adjustable headband strap are connected to lower sections conforming to the acupuncture points located around the temporomandibular joint of the jaw. Further, the headband device has additional acupuncture points located at the base of the skull behind the ear. In one embodiment, the headband strap comprises a head strap for fitting about or around the wearer's head, a temple strap extending downwardly from the headband strap engages the wearer's chin and conforms to the acupuncture points located around the temporomandibular joint of the wearer's jaw, an ear strap or ear flap extending downwardly from the headband strap adapted to conform at a base of a skull behind the wearer's ear.

In another embodiment, a smart-phone app could control the unit for ultimate operability, portability, and ease of use. In an embodiment, the device comprises back adjustment connectors. Further, the adjustable strap could consist of a shoulder extension, and face and head extensions. In some embodiments, the extensions could cover several acupuncture points located on the head, face, and back of the shoulders respectively, for a more complete therapy. In an embodiment, each extensions as well as those built into the adjustable headband strap, offer a combined TENS and red LED contact points.

In an aspect, the adjustable head strap is provided with the extensions. The acupuncture points are fitted with LEDs near the temporomandibular joint of the jaw and on the backside of the ear. In one embodiment, the temple strap consists of a TENS electrode and LED Unit. In an embodiment, the headband device is adjusted to fit snugly on the head and under the chin. The LEDs illuminate various acupuncture points on the face and neck. The TENS connectors lay flat against the headband strap. In an embodiment, the LEDs project from the band toward the skin. In another embodiment, the LEDs could be powered with 2 AA replaceable batteries in the housing. A TENS input connector is mounted near the battery housing on the adjustable headband strap. Two ear flaps could be located on the LEDs on the acupuncture points just below and in front of the ear.

In an embodiment, the TENS connectors connect the remote TENS controller to the headband strap and the headband strap to the user's skin for the optimum stimulation. The flexible wires from the headband to the TENS electrodes could allow the user to wear the headband device and the TENS connections in total comfort, without binding or having to re-adjust lead location often. The end of the headband leads has a clip, which allows quick exchange of the TENS electrodes, if the gel contact becomes compromised. In another embodiment, the optimum application of the TENS signal requires 2 skin contact TENS electrodes located not more than 1.5" apart. Each of the TENS connectors is marked and the mating leads are stored in an electrode/lead organization box.

In yet another embodiment, the TENS leads and TENS electrodes are longer and shorter depending upon where they are to be used; for example: those are used in shoulder could be about 18" long and the ones used near the rear neck could be about 6" long. The TENS input connector feed is polarized and has slightly larger diameter pins so it cannot be placed in any of the TENS output connectors. In further embodiment, TENS leads on the left and right neck are manufactured with optimum length and could lead to reach acupuncture points. The TENS leads could be optimized to reach from the headband device to the body site with just a little slack to allow unrestricted head movement, etc.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

FIG. 7A is the front view of the TENS controller, in accordance with the present invention.

FIG. 7B is the side view of the TENS controller, in accordance with the present invention.

DETAILED DESCRIPTION OF EMBODIMENTS

A description of embodiments of the present invention will now be given with reference to the Figures. It is expected that the present invention may be embodied in other specific forms without departing from its spirit or essential characteristics. The described embodiments are to be considered in all respects only as illustrative and not restrictive.

Figure 1:
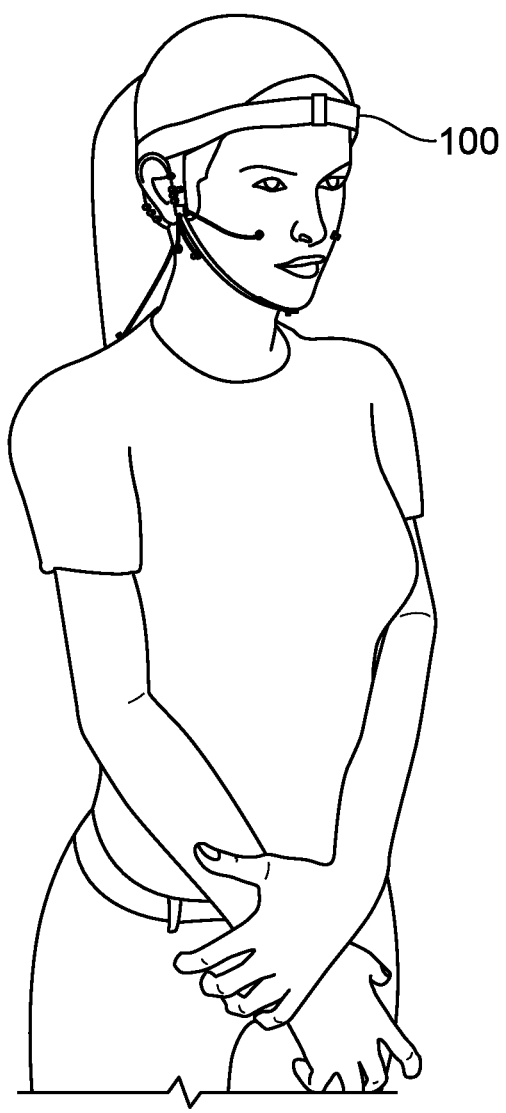
FIG. 1 shows a perspective view of an end user or wearer using a headband device, in accordance with the present invention.
Figure 2A:
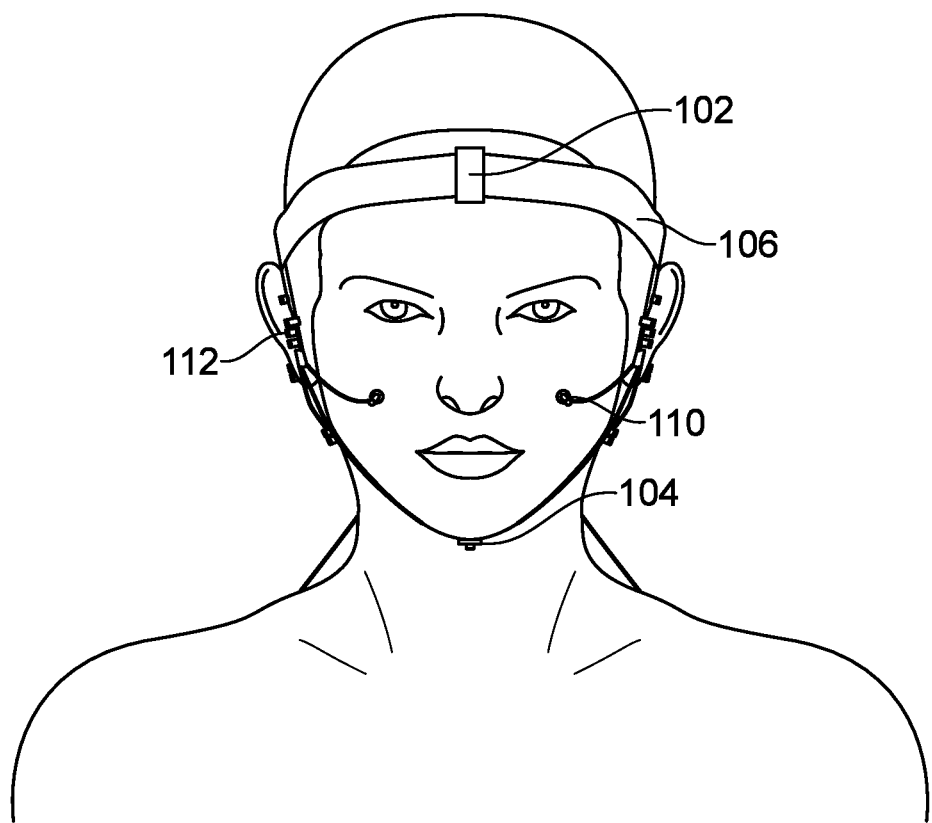
FIG. 2A shows a front perspective view of an end user using the headband device, in accordance with the present invention.
Figure 2B:
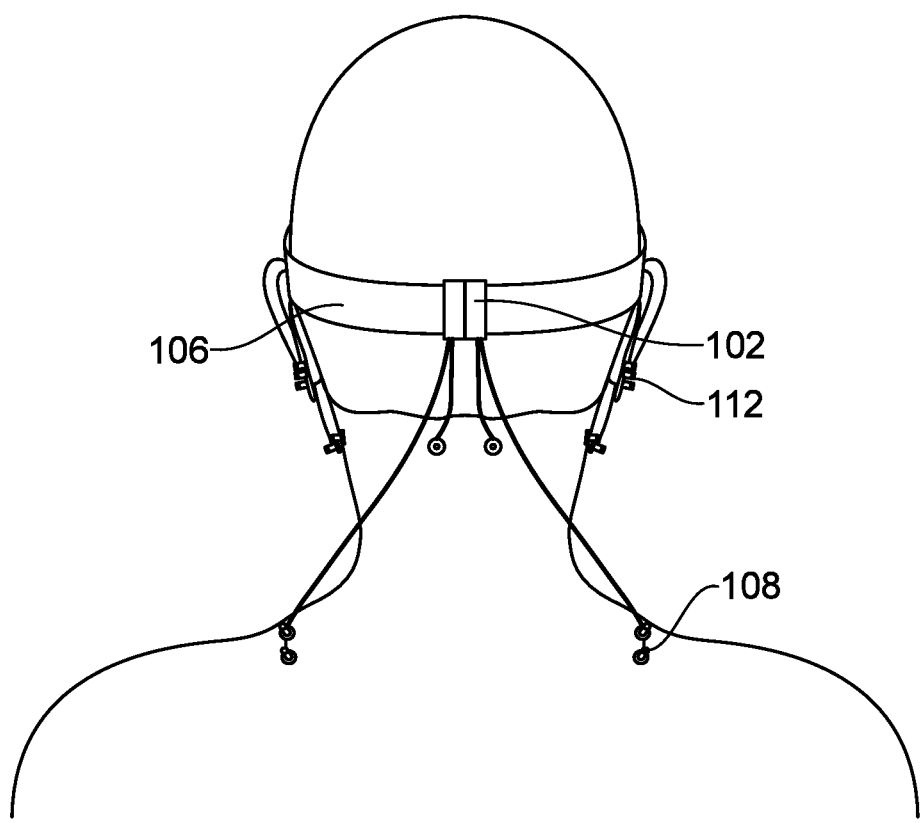
FIG. 2B shows a back perspective view of an end user using the headband device, in accordance with the present invention.
Figure 2C:
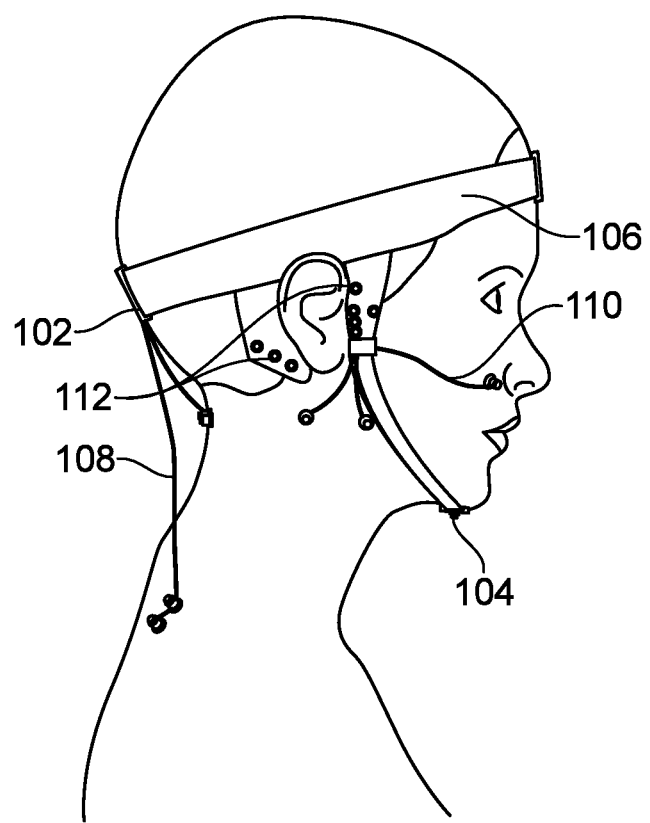
FIG. 2C shows a side perspective view of an end user using the headband device, in accordance with the present invention.

Referring to FIG. 1, a perspective view of an end user or wearer using a headband device 100 is disclosed. The adjustable headband device 100 is a solution for combining the benefits of LED therapy with the stimulation and pain-relieving qualities of a TENS unit 136 (shown in FIG. 7B) for the TMJ treatment. Referring to FIG. 2A, a front perspective view of an end user using the headband device 100 in accordance with the present invention is disclosed. The device 100 is completely portable and wearable. The adjustable headband strap 106 of the headband device 100 could be worn while doing daily tasks and almost anywhere. The device 100 straps on to the head with a comfortable expandable/adjustable headband strap 106 that wraps around the circumference of the wearer's head. In an embodiment, adjustment connectors 102 are located at the front and backside of the adjustable TMJ Headband device 100 that could allow the user or wearer to adjust the size of the headband. In one embodiment, the adjustable headband strap 106 could be modified to fit from a small child size increasingly up to a large adult size. In an embodiment, the adjustable headband strap 106 are connected to lower sections conforming to the acupuncture points 112 located around the temporomandibular joint of the jaw. Further, the headband device 100 has additional acupuncture points 112 located at the base of the skull behind the ear. In one embodiment, addition to the acupuncture points 112 on the headband device 100, a set of extensions 108 and 110 are available that will plug into the adjustment connectors 102 on the adjustable headband strap 106. In another embodiment, a smart-phone app could control the unit for ultimate operability, portability, and ease of use. Referring to FIG. 2B shows a back perspective view of an end user using the headband device 100 is disclosed. In an embodiment, the back adjustment connectors 102 is illustrated. Further, the adjustable strap 106 could consist of a shoulder extension 108. FIG. 2C shows a side perspective view of an end user using the headband device 100, in accordance with the present invention. In some embodiments, the extensions 108 and 110 could cover several acupuncture points 112 located on the head, face, and back of the shoulders respectively, for a more complete therapy. In an embodiment, each extension 108 and 110, as well as those built into the adjustable headband strap 106, offer a combined TENS and red LED contact points.

In one embodiment, the headband strap 106 comprises a head strap for fitting about or around the wearer's head, a temple strap extending downwardly from the headband strap 106 engages the wearer's chin and conforms to the acupuncture points 112 located around the temporomandibular joint of the wearer's jaw, an ear strap extending downwardly from the headband strap 106 adapted to conform at a base of a skull behind the wearer's ear. In one embodiment, at least one adjustment connector 104 is disposed at the temple strap to vary the size of the temple strap.

Figure 3A:
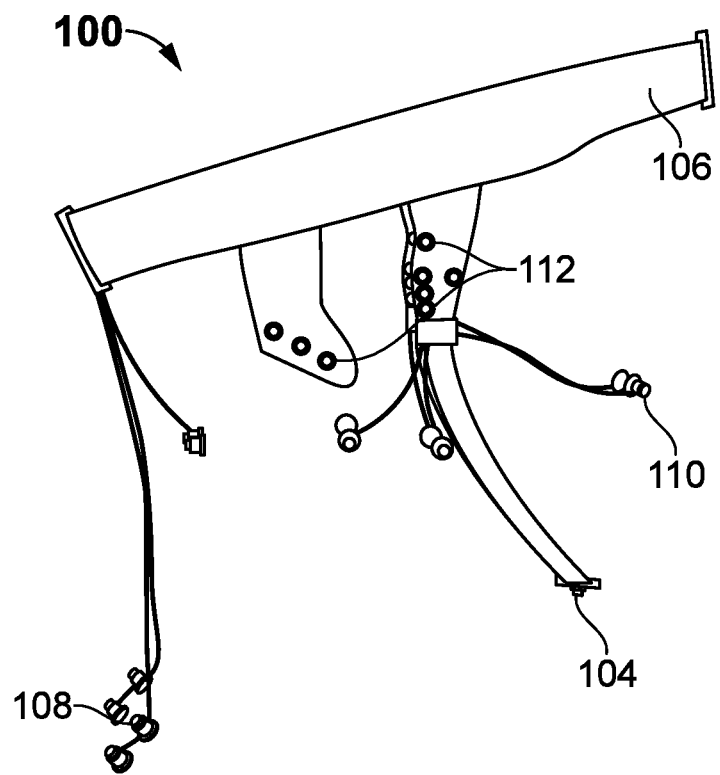
FIG. 3A shows a side perspective view of the headband device, in accordance with the present invention.
Figure 3B:
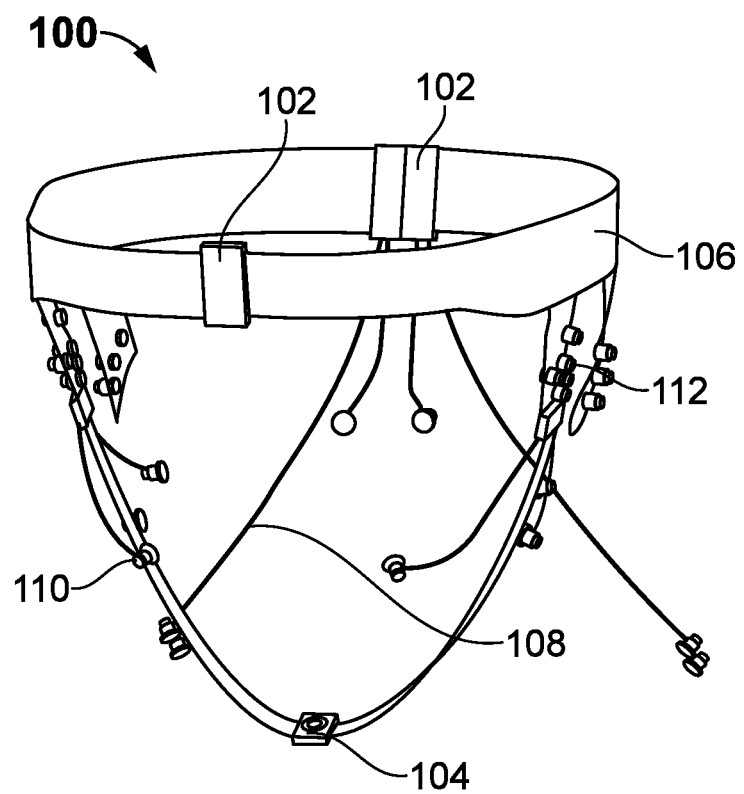
FIG. 3B shows a front perspective view of the headband device, in accordance with the present invention.

Referring to FIG. 3A, a side perspective view of the headband device 100 is shown in which the adjustable head strap 106 is illustrated with the extensions 108 and 110. The acupuncture points 112 are fitted with LEDs 114 near the temporomandibular joint of the jaw and on the backside of the ear. FIG. 3B shows a front perspective view of the headband device 100, in accordance with the present invention. In one embodiment, the temple strap consists of a TENS electrode 120 and LED Unit. In an embodiment, shoulder extensions 108, and face and head extensions 110 provide combined TENS and red LED contact points.

Figure 4:
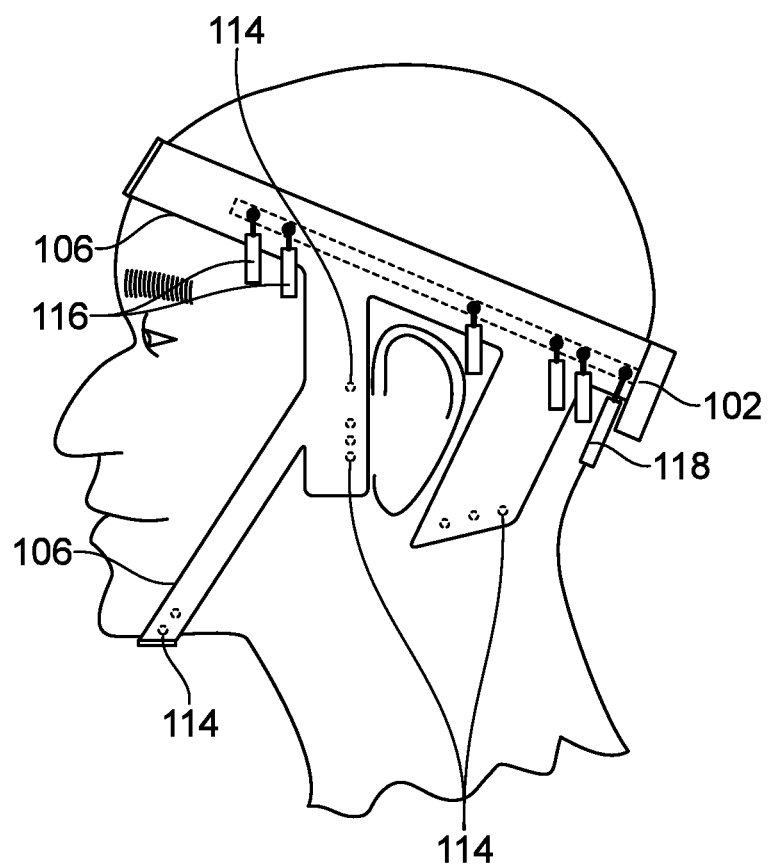
FIG. 4 shows a side view of the different components used in the headband device, in accordance with the present invention.

FIG. 4 shows a side view of the different components used in the headband device 100, in accordance with the present invention. In an embodiment, the headband device 100 is adjusted to fit snugly on the head and under the chin. The LEDs 114 illuminate various acupuncture points 112 on the face and neck. The TENS connectors 116 lay flat against the headband strap 106. In an embodiment, the LEDs 114 project inward from the band toward the skin 124. In another embodiment, the LEDs 114 could be powered with 2 AA replaceable batteries in the housing. The TENS input connector 118 is mounted near the battery housing on the adjustable headband strap 106. There is one for each side of the headband. The 2 ear flaps or ear straps could be located on the LEDs 114 on the acupuncture points 112 just below and in front of the ear.

Figure 5:
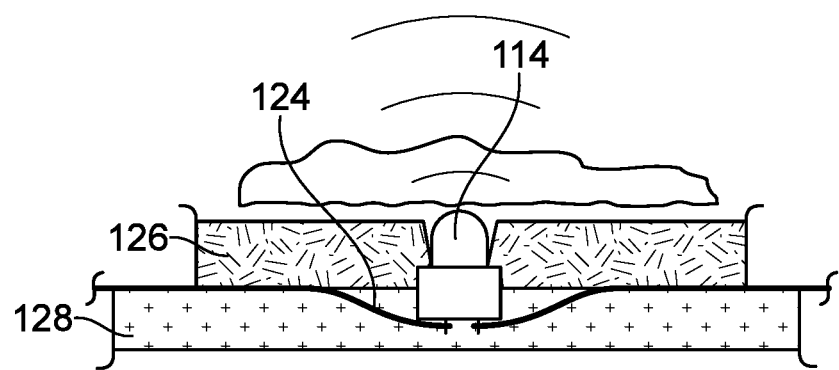
FIG. 5 illustrates an arrangement of LED inside the headband device, in accordance with the present invention.

FIG. 5 illustrates an arrangement of LEDs 114 inside the headband device 100, in accordance with the present invention. In an embodiment, the adjustable headband strap 106 is sewn from Lycra® fabric 128 as the outer layer. This is stretchy and soft to the feel. The Lycra® fabric 128 is woven from 40% polyurethane and 60% cotton fibers. This Lycra® fabric 128 could be supplied in almost any vibrant color. In an embodiment, the Kapton flexible circuit of the TENS device and the low voltage wires connecting the LEDs 114 are sandwiched between the layer Lycra® 128 on the outside and a thin layer of medical grade EVA foam 126. The LEDs 114 are located in headband strap 106 where they project the light toward the acupuncture points 112 in front and below the ear. The EVA foam 126 layer is adhesively bonded to the Lycra® 128 and the edge turned under and sewn to provide high quality headband strap 106 with nicely finished edges. In another embodiment, the headband strap 106 is adjustable using a hook and loop (H&L) fastener that is sewn to the front of the headband and under the chin. These H&L fasteners allow only one size to be required for adult and teen wearers. After the sewing is completed the battery pack is attached to the back of the headband and the appropriate connections made for the LEDs 114 and the TENS connectors 116.

In further embodiment, the stretch Lycra fabric 128 is located on the outside of the headband strap 106 and could be any vibrant color. The LED 114 is powered using the wires imbedded between the EVA foam 126 and Lycra fabric layer 128. The red light is projected in a 120-degree solid angle directly into the face to stimulate the skin 124 and cells. The medical grade EVA foam 126 shields the LED 114 and allows it to gently rest against the skin 124 for better light penetration.

Figure 6:
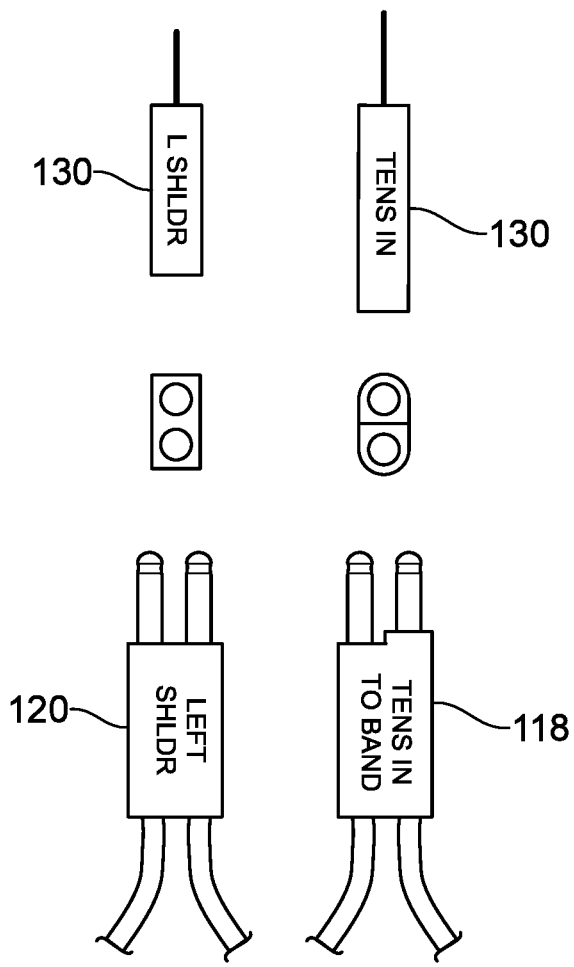
FIG. 6 illustrates TENS connectors used in the headband device, in accordance with the present invention

FIG. 6 illustrates TENS connectors 116 used in the headband device 100, in accordance with the present invention. In an embodiment, the TENS connectors 116 connect the remote TENS controller 132 to the headband strap 106 and the headband strap 106 to the user's skin 124 for the optimum stimulation. The flexible wires from the headband to the TENS electrodes 120 could allow the user to wear the headband device 100 and the TENS connections in total comfort, without binding or having to re-adjust lead location often. The ends of the headband leads have a clip, which allows quick exchange of the TENS electrodes 120 if the gel contact becomes compromised. In an embodiment, the TENS leads 130 when not in use, are stored in the plastic case as are several replacement TENS electrodes 120. In another embodiment, the optimum application of the TENS signal requires 2 skin contact TENS electrodes 120 located not more than 1.5" apart. Each of the TENS connectors 116 is marked and the mating leads are stored in an electrode/lead organization box.

In yet another embodiment, the TENS leads 130 and TENS electrodes 120 are longer and shorter depending upon where they are to be used; for example: those are used in shoulder could be about 18" long and the ones used near the rear neck could be about 6" long. The TENS input connector 118 feed is polarized and has slightly larger diameter pins so it cannot be placed in any of the TENS output connectors. In further embodiment, TENS leads 130 on the left and right neck are manufactured with optimum length, that could lead to reach acupuncture points 112. The TENS leads 130 could be optimized to reach from the headband device 100 to the body site with just a little slack to allow unrestricted head movement, etc.

Preferably, the present invention consists of a TENS controller 132 as illustrated in FIG. 7A and FIG. 7B. Basically, transcutaneous electrical nerve stimulation (TENS) system consists of 3 basic components such as; TENS controller 132, TENS connector 116, and TENS lead 130 and TENS electrode 120. In an embodiment, the TENS controller 132 is a small unit, manufactured with a rubber and plastic case and could be operable using the buttons and touch screen. The compact device TENS controller 132 could be placed in the pocket or could be clipped onto the belt. The TENS controller 132 has a rechargeable battery and operates 2 channels of electrical pulses independently. The user stimulates the jaw area on one side and the neck area on the other at the same time, using differ frequencies, modes and amplitude of signals, while continuing the red light therapy. In another embodiment, the TENS controller 132 could provide 5 modes of operations, such as: burst normal, modulation, strength duration1, and strength duration2. Further, the user is able to set the frequency, amplitude, and time of operation of the TENS controller 132. The memory of the TENS controller 132 could hold multiple past sessions and could repeat any of them as requested.

In an embodiment, the TENS connectors 116 are soldered to the flexible circuit prior to assembly and are fed through the Lycra fabric 128 at the outer layer. The wire of the TENS connectors 116 is reinforced with hot melt adhesive of fabric matching color. Each of the TENS connectors 116 could be marked with the appropriate legend for the user to select the matching wires and electrodes for use. The right and left hemisphere are isolated for the optimum in therapy to allow the TMJ pain to be treated on both sides independently.

In an embodiment, the TENS controller 132 could apply electronic nerve stimulation for pain management and to improve rehabilitation speed. In another embodiment, the TENS controller 132 could be used by buttons or touch screen while using the optional App on the user's smartphone. Further, the TENS controller 132 could drive 4 electrodes at one time with each channel of 2 electrodes under individual control. The lead wire 138 could plug into each channel outlet on the TENS controller 132 and then runs to the left or right side of the headband device 100, plugging into the polarized adjustment connectors 102 in the headband device 100. The TENS controller 132 could be placed in the pocket or clipped onto the belt and the channel feed wires are long enough to allow comfortable movement of the head and adjustable headband strap 106 without binding. The TENS battery 134 of the TENS controller 132 could be recharged using an USB connector and an AC to DC adapter. The system starts beeping when the TENS battery 134 needs to be discharged or the TENS electrodes 120 are not able to make acceptable contact.

Figure 8A:
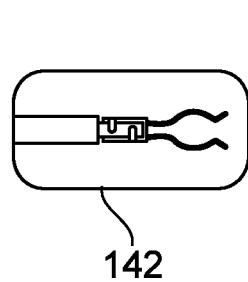
FIG. 8A is the top view of the supplied electrode, in accordance with the present invention.
Figure 8B:
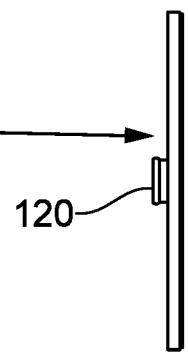
FIG. 8B is the side view of the supplied electrode, in accordance with the present invention.
Figure 8C:
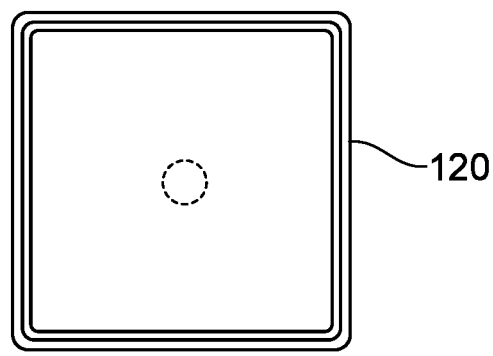
FIG. 8C is a perspective view of the supplied electrode, in accordance with the present invention.

Preferably, the present invention consists of TENS electrodes 120 as in FIGS. 8A, 8B and 8C. As shown in the FIG. 8B, the TENS electrode 120 is a 1.5" square unit, that clips onto the TENS leads 130 from the headband strap 106. A clip 142 is soldered onto the TENS leads 130 and is clipped onto the snap on the TENS electrode 120. Further, as shown in the FIG. 8C; the 4 layered TENS electrodes 120 conducts the electrical signal from the lead through the electrode 120 to the skin 124. The final layer of the TENS electrode 120 is a firm gel layer that touches the skin 124 for optimum conduction. In one embodiment, the TENS electrode 120 is easy to replace if the gel layer becomes worn out or contaminated. The gel layer is not soft like Vaseline and is not messy. The outer edge of the TENS electrode 120 has repositionable adhesive to allow more than one use.

Figure 9:
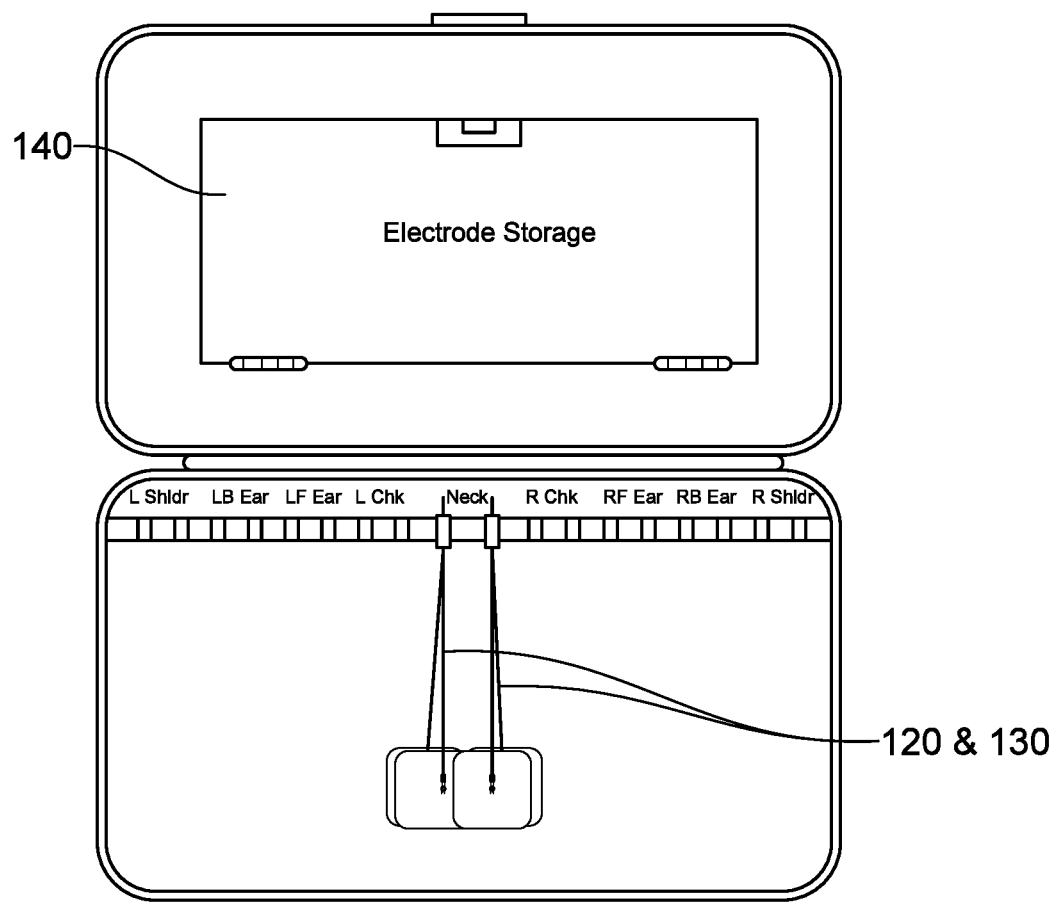
FIG. 9 illustrates lead and electrode container, in accordance with the present invention.

FIG. 9 illustrates TENS lead 130 and electrode 120 container, in accordance with the present invention. In an embodiment, molded plastic case snaps shut to retain the TENS electrode 120 and TENS leads 130 in an organized and clean format. A hinged door 140 snaps shut and retains new electrodes in an easily accessible location. When the upper section is closed over the lower section, the leads are pressed down into the foam bar and retained.

Further, the headband device 100 has been fabricated to allow the combination of both red light and TENS therapy in one, easy to use, comfortable appliance. In an embodiment, the fabric and foam headband device 100 has built-in LEDs 114 and are located over the acupuncture points 112 in and around the ear, with additional lighting under the chin. The headband device 100 also is a suspension appliance for the TENS connectors 116, allowing freedom for the user to combine TENS pain relief and cellular rehabilitation with the red light therapy. The headband device 100 is light in weight so the user can wear it and the TENS unit 136 leads while going about normal tasks in the home or even driving. The LEDs 114 are powered with replaceable AA batteries, which are turned on using the tactile membrane switch on the battery holder. The TENS controller 132 is placed in the pocket or suspended on the belt and the leads with electrodes are placed in the mating connectors. After electrode placement on the appropriate pain control locations, the TENS controller 132 can be engaged and used to reduce the pain. After use, the TENS leads 130 can be unclipped and re-stored in the protective carrying case.

The headband device 100 is a combination of Red LED and TENS therapy and made up of comfortable headband of expandable material. The headband device 100 could be available for all sizes ranging from children to adults. Further, the said device 100 relieves TMJ pain and promotes healing. The device 100 is built with acupuncture points 112 on both facial and back region. The said device 100 could promote facial re-invigoration and stimulation. The headband device 100 could be operated through a smart-phone app control. The device 100 is portable to carry anywhere and could be operated both as plug in power supply and with battery.

Preferred embodiments of this invention are described herein, including the best mode known to the inventors for carrying out the invention. It should be understood that the illustrated embodiments are exemplary only, and should not be taken as limiting the scope of the invention.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein.

What is claimed is:

1. A therapeutic device for treating temporomandibular joint disorder, comprising:
 a headband strap comprising:
  a head strap fitting configured around a wearer's head,
  a temple strap configured to extend downward from the headband strap engages the wearer's chin and conforms to one or more acupuncture points located around the temporomandibular joint of the wearer's jaw,
  an ear strap configured to extend downward from the headband strap adapted to conform at a base of a skull behind the wearer's ear, and
 one or more extension members configured to conform onto the acupuncture points located on the wearer's head, face, and back of the shoulder, and
 a transcutaneous electrical nerve stimulation (TENS) device and a light emitting diode (LED) device having a contact point being disposed at a location of the headband strap and extension members conforming to the acupuncture points of the wearer configured to provide electronic nerve stimulation and emit red light to the acupuncture points.

2. The device of claim 1, wherein the head strap comprises at least two adjustment connectors and the temple strap comprises at least one adjustment connectors.

3. The device of claim 2, wherein the at least two adjustment connectors of the head strap is configured to vary the circumference of the head strap.

4. The device of claim 2, wherein the adjustment connector of the head strap is disposed at a rear side and front side of the head strap.

5. The device of claim 2, wherein the adjustment connector of the temple strap is configured to vary the size of the temple strap.

6. The device of claim 1, wherein the extension members extend from the at least two adjustment connectors of the head strap.

7. The device of claim 1, wherein the device is controlled by a user device via a software application.

8. The device of claim 1, further comprising a remote TENS controller in communication with a TENS connector.

9. The device of claim 8, wherein the TENS connector is in communication with the TENS electrodes and TENS leads.

10. The device of claim 8, wherein the TENS controller is configured to operate at least one of a burst normal, modulation, strength duration1, and strength duration2 mode of operation.

11. The device of claim 1, wherein the contact point comprises a LED, TENS electrode and TENS lead.

12. The device of claim 11, wherein the LED projects from the headband strap towards the wearer skin to emit light towards the acupuncture points.

13. The device of claim 11, wherein the LED is configured to project red light in a 120-degree solid angle.

14. The device of claim 11, wherein the TENS electrode is configured to conduct an electrical signal from the TENS lead to the TENS electrode for pain management and rehabilitation rapidity.

15. The device of claim 11, wherein the TENS electrode comprises a firm gel layer configured to contact the skin for optimum conduction of the electrical signal.

16. The device of claim 11, wherein the TENS controller is configured to provide two independent channels of electrical pulses.

17. The device of claim 16, wherein each of the channels of electrical pulses is configured to drive at least two TENS electrodes.

18. The device of claim 1, further comprising one or more rechargeable batteries.

19. The device of claim 1, further comprising one or more buttons and a touch interactive user interface to operate the device.

20. The device of claim 19, wherein the device further enables the wearer to set frequency, amplitude, and time of operation of the device via the user interface.

* * * * *